(12) United States Patent
Lee et al.

(10) Patent No.: US 7,628,531 B2
(45) Date of Patent: Dec. 8, 2009

(54) METHODS AND APPARATUS FOR DUAL SOURCE CALIBRATION FOR DISTRIBUTED TEMPERATURE SYSTEMS

(75) Inventors: Chung E. Lee, College Station, TX (US); Kent Kalar, Austin, TX (US); Michael E. Sanders, Austin, TX (US)

(73) Assignee: SensorTran, Inc, Austin, TX (US)

( * ) Notice: Subject to any disclaimer, the term of this patent is extended or adjusted under 35 U.S.C. 154(b) by 194 days.

(21) Appl. No.: 11/685,637

(22) Filed: Mar. 13, 2007

(65) Prior Publication Data

US 2007/0223556 A1 Sep. 27, 2007

Related U.S. Application Data

(60) Provisional application No. 60/781,833, filed on Mar. 13, 2006, provisional application No. 60/787,617, filed on Mar. 30, 2006.

(51) Int. Cl.
*G01K 15/00* (2006.01)
*G01K 3/00* (2006.01)
*G01K 11/00* (2006.01)
*G01J 5/00* (2006.01)

(52) U.S. Cl. .................. 374/1; 374/161; 374/131; 374/121; 374/137

(58) Field of Classification Search .......... 374/1, 374/131, 121, 161, 130, 137, 2
See application file for complete search history.

(56) References Cited

U.S. PATENT DOCUMENTS 4,823,166 A * 4/1989 Hartog et al. ............... 356/44
5,113,277 A 5/1992 Ozawa et al. ............... 359/127
5,592,282 A * 1/1997 Hartog ........................ 356/44
5,639,162 A * 6/1997 Sai ............................. 374/161
5,765,948 A * 6/1998 Sai ............................. 374/161
5,928,222 A * 7/1999 Kleinerman ................. 606/16
7,057,714 B2 6/2006 Fredin et al. ............... 356/73.1
7,250,972 B2 * 7/2007 Oshima ....................... 348/335
7,284,903 B2 * 10/2007 Hartog ........................ 374/130
2005/0140966 A1 6/2005 Yamate et al. .............. 356/72.1
2006/0210269 A1 * 9/2006 Farhadiroushan et al. ..... 398/48

FOREIGN PATENT DOCUMENTS

WO 2004/104536 12/2004

OTHER PUBLICATIONS

"Spinoff 2006: Innovative Partnerships Program" by the National Aeronautics and Space Administration Center for AeroSpace Information (CASI) pp. 94-97, 2006.

* cited by examiner

*Primary Examiner*—Gail Verbitsky
*Assistant Examiner*—Mirellys Jagan
(74) *Attorney, Agent, or Firm*—M A. Ervin & Associates; Michael A. Ervin (57) ABSTRACT

Systems and methods for calibrating a temperature sensing system are disclosed. In one respect, a dual light source configuration may be provided. A first light source may illuminate a sensing fiber and an anti-Stokes band may be detected. A second light source may illuminate a sensing fiber and a Stokes band may be detected, where the Stokes band is substantially similar to the anti-Stokes band of the first light source. A ratio between the anti-Stokes and Stokes band may be used to calibrate a temperature sensing system.

3 Claims, 10 Drawing Sheets

METHODS AND APPARATUS FOR DUAL SOURCE CALIBRATION FOR DISTRIBUTED TEMPERATURE SYSTEMS

This application claims priority to provisional patent application Ser. No. 60/781,833 filed on Mar. 13, 2006 and Ser. No. 60/787,617 filed Mar. 30, 2006. The entire text of each of the above-referenced disclosures, including figures, is specifically incorporated by reference herein without disclaimer.

BACKGROUND OF THE INVENTION

1. Field of the Invention

The present invention relates generally to temperature sensing. More particularly, the present disclosure relates to systems for calibrating temperature profiles in, for example, a distributed line system.

2. Description of Related Art

Optical fibers have been used for optical communication for decades. Recently, optical fiber sensing technologies have grown rapidly due to fiber advantages, which conventional electrical sensors do not have. The advantages of fiber include the ability to handle much higher bandwidth and inherently safe operation (no generation of electric sparks). Also optical fiber is inherently immune to EMI (ElectroMagnetic Interference), and it does not radiate EMI. A prominent feature of the fiber is the capability of true distributed parameter measurement. Utilizing this technology, temperature and strain profiles along significant distances can be monitored over extended lengths. Many temperature data points can be processed along a considerable length, over tens of kilometers. The resultant distributed measurement is equivalent to numerous conventional point temperature sensors which would require more deployment equipment and a higher operational costs.

When an optical fiber is excited with a laser light with a center wavelength $\lambda$, most of the light may be transmitted but small portions of incident light $\lambda$ are scattered backward and forward along the fiber. Scattered light is categorized into three bands: Rayleigh, Raman, and Brillouin scatterings. For the measurement of distributed temperatures, a few components may be used such as a Rayleigh scattering, which is the same as an excitation wavelength $\lambda$, and a Stokes and anti-Stokes components which are longer and shorter than $\lambda$, respectively. These three components may be separated by optical filters and received by the photo detectors to convert the light to electrical signals. The ratio of temperature sensitive anti-Stokes intensity to temperature insensitive Rayleigh or Stokes intensities may be used for temperature measurement.

To obtain a local temperature profile along a distance, two methods—time domain approach and frequency domain approach have—been applied conventionally. The time domain method uses a pulsed light source and the position of the temperature is identified by the calculation of the pulse round trip time to the distance under test. The frequency method uses a modulated laser source and the position can be calculated by applying the inverse Fourier transformation of a sensing fiber's transfer function or frequency response.

U.S. Pat. No. 5,113,277, which is incorporated by reference, discloses a Fiber Optic DTS (Distributed Temperature Sensing) system, which involves a pulsed light source and a temperature measurement was made by the ratio between Stokes and anti-Stokes intensities at each measured distance determined from the roundtrip time of the pulse. U.S. Pat. No. 7,057,714, which is incorporated by reference, discloses a stepped modulation method to sweep the frequency of the laser source. The time domain profiles of Stokes and anti-Stokes attenuations are obtained by applying the inverse Fourier transformation of amplitude and phase responses of each modulating frequency component. The time domain method is simpler than frequency domain analysis but it requires a costly pulsed light source and higher data acquisition components but has a lower signal to noise characteristics.

The temperature profile along the sensing fiber in DTS is obtained by the ratio of the temperature insensitive Stokes to temperature sensitive anti-Stokes backscattered intensities from a deployed sensing fiber as described above. But both scattering intensities are also dependent on, for example, mechanical and chemical perturbations such as micro bends, tensions, compressions and chemical ingressions such as hydrogen gas, which are common in an oil field environment under high temperatures and high pressures. This kind of ambiguity, i.e., whether the scattering intensities are made by pure local temperature effect or by other effects mentioned above particularly in an anti-Stokes profile, usually introduces some errors in the temperature calculation and needs to be corrected to generate more accurate temperature measurements. This ambiguity may be corrected with the aid of conventional optical reflectometry methods, in which the back-scattered light provides a measure of wavelength dependant attenuations. In order to implement this idea to the DTS system, an extra incident source with the same wavelengths and similar line width of anti-Stokes or Stokes bands is required. Commercial availability and/or the cost have been major obstacles for a practical implementation of this correction technique.

The referenced shortcomings above are not intended to be exhaustive, but rather are among many that tend to impair the effectiveness of previously known techniques for temperature profiling; however, those mentioned here are sufficient to demonstrate that the methodologies appearing in the art have not been altogether satisfactory and that a significant need exists for the techniques described and claimed in this disclosure.

SUMMARY OF THE INVENTION

The present disclosure provides an economic and straightforward solution for determining an accurate temperature profile in a distribution line system, and more particularly for correcting error generated by the ambiguities of a local sensing fiber cable. Embodiments of this disclosure utilize a secondary light source whose Stokes band coincides with the anti-Stokes band of a primary light source of the DTS system.

In one respect, a method is provided. The method may provide a first and second light source. The first light source may be configured to operate in a measurement mode and the second light source may be configured to operate in a correction mode. The second light source may have a Stoke band substantially similar to the anti-Stoke band of the first light source. A ratio between the anti-Stoke band and Stoke band may be used to calibrate a temperature sensing system.

In some respects, a sensing fiber may be illuminated with a first light source and an anti-Stoke band may be detected. Similarly, the sensing fiber may be illuminated with a second light source and a Stokes band may be detected. A ratio between the detected Stokes band and anti-Stokes band may be used to calibrate a temperature sensing system.

The terms "a" and "an" are defined as one or more unless this disclosure explicitly requires otherwise.

The term "substantially," "about," and its variations are defined as being largely but not necessarily wholly what is specified as understood by one of ordinary skill in the art, in one non-limiting embodiment substantially and its variations refers to ranges within 10%, preferably within 5%, more preferably within 1%, and most preferably within 0.5% of what is specified.

The term "coupled" is defined as connected, although not necessarily directly, and not necessarily mechanically.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF THE ILLUSTRATIVE EMBODIMENTS

The disclosure and the various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

The present disclosure provides techniques for improving the accuracy of distributed temperature measurements derived from the intensities of back scattered wavelengths along a sensing fiber in a distributed fiber temperature sensing instrument. Optical attenuation along the optical fiber sensing cable may be empirically derived for the light wavelengths of interest and may be used to obtain an improved temperature calculation. An apparatus of the present disclosure integrates fiber with two or more different incident wavelengths. The wavelength values are chosen so the anti-Stokes Raman return of the primary light source is substantially the same value as the Stokes Raman return of the secondary light source. This Raman Stokes backscatter may be used as indicator of fiber attenuation profile for the primary light source's anti-Stokes wavelength.

In one respect, the present disclosure covers both a time domain method which uses optical pulsed light sources (for the first and second light sources) and a frequency domain method, which is based on other types of modulation known in the art of the first and second light sources.

Figure 1:
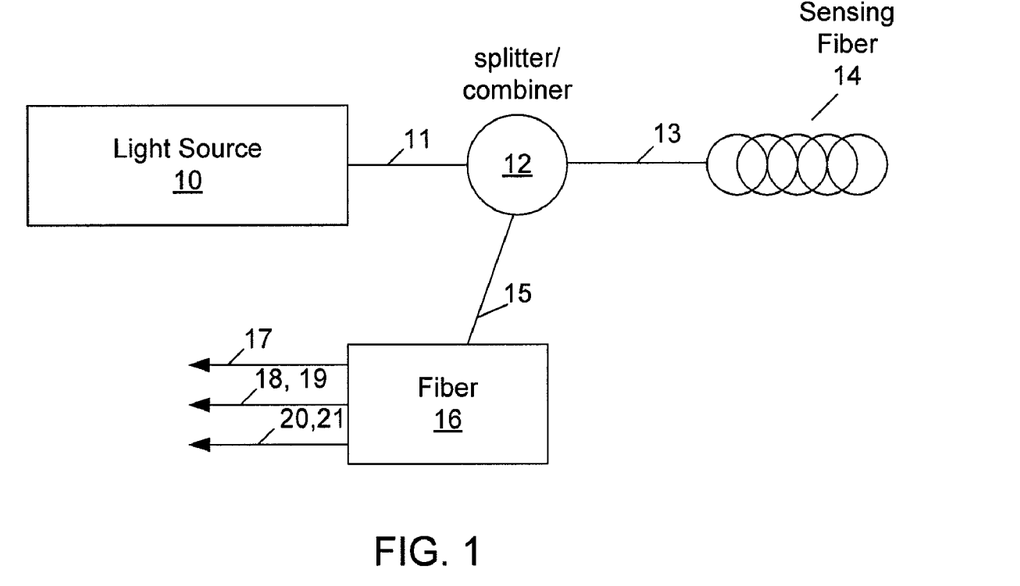
FIG. 1 shows a block diagram of a distributed temperature sensing system.

Referring to FIG. 1, a basic configuration of a DTS system based on light scattering is shown. The light source 10 is injected into a lead fiber 11 to reach the sensing fiber 14 through a light splitter/combiner 12, which is coupled to sensing fiber 14. When the light is guided to a sensing fiber, a portion of the light is scattered and travels to a wavelength selector 16 through a splitter/combiner 12 again via lines 13 and 15, respectively. The backscattered light from fiber 16 may include a Raleigh component 17 (same center wavelength as injected light), a Brillouin component 18, 19 and a Raman scattering component 20, 21. The latter two may be shifted from the input wavelength and have mirrored images symmetrical to the two components called Stokes and anti-Stokes.

Figure 2:
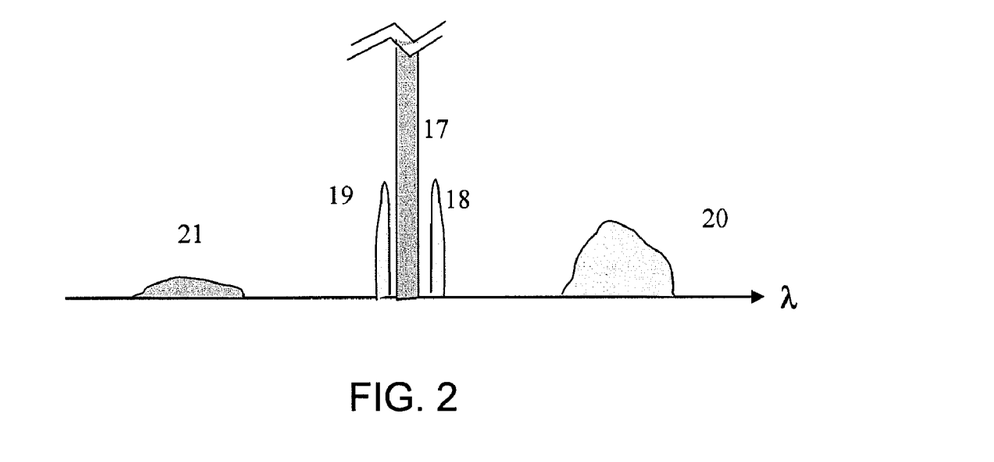
FIG. 2 shows scattering components from the distributed temperature sensing system of FIG. 1.

Among these scatterings, Raleigh component 17 and Raman components 20 (Stokes) and 21 (anti-Stokes) are used for the calculation of temperature profile. The Stokes and anti-Stokes band may be separated by more than tens of nanometers but Brillouin components are more closely spaced—less than about 0.1 nm from the Rayleigh bandwidth. These components are shown in FIG. 2.

Figure 3:
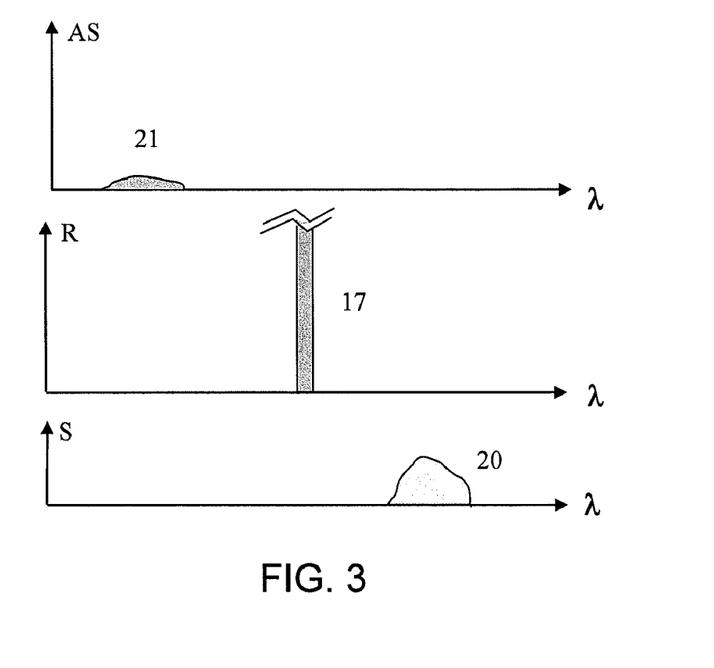
FIG. 3 shows a corresponding output of the components of FIG. 2 from an optical wavelength separation assembly.

To calculate the temperature profile, back scattered light components may be fed to an optical wavelength separation assembly 16, and the light may be separated to three groups, anti-Stokes (AS), Rayleigh (R), and Stokes (S). The output of each group, shown in FIG. 3, may subsequently be guided to three optical converters to convert each group's optical signal to electrical signals to the signal processing unit.

As mentioned before, the temperature profile may be calculated by the ratio of Stokes to anti-Stokes component. But the intensities of both components may be affected by local circumstances and the variation of these intensities may be compensated or calibrated to achieve a more accurate temperature measurement. Particularly, the magnitude of anti-Stokes band may be varied by temperature as well as other physical perturbations other than temperature. Therefore, there is a need for common perturbations to be eliminated. For this purpose, a temperature independent Rayleigh component may be used as a reference. But the separation between Rayleigh and anti-Stoke band is typically more than about 50 nm, hence, a precise compensation is difficult. For accurate correction, another light source with a same band of anti-Stokes is useful.

Figure 4:
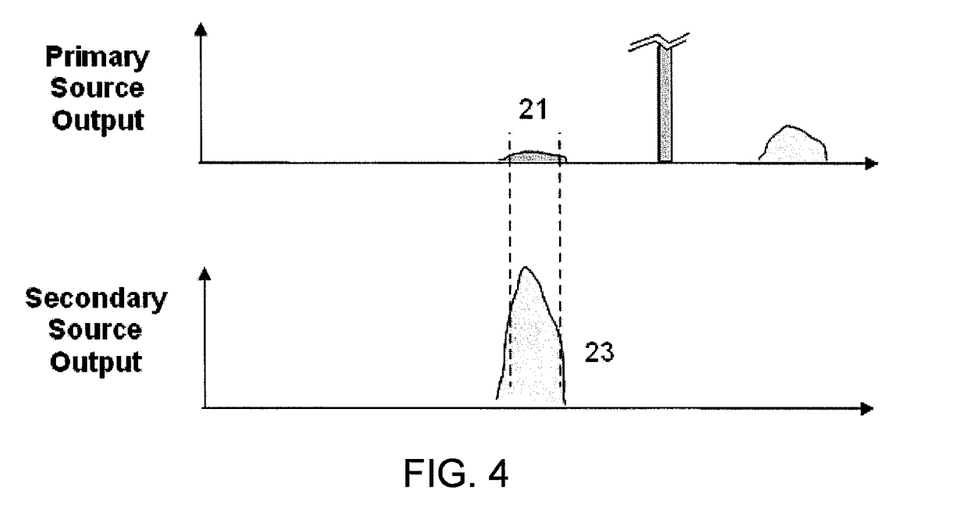
FIG. 4 shows a wavelength diagram of a distributed temperature sensing system, in accordance with embodiments of the disclosure.
Figure 5:
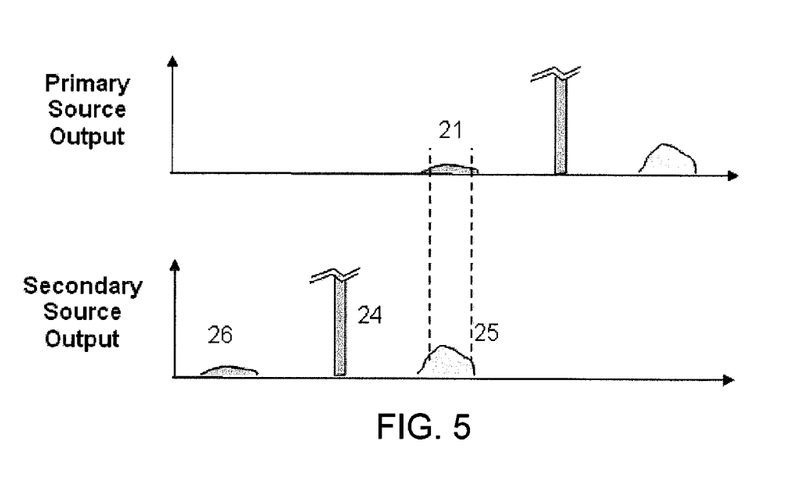
FIG. 5 shows a graph of scattering bands of a primary light source and a secondary light source, in accordance with embodiments of the disclosure.

Referring to FIG. 4, a diagram is shown of a scattering component 23 of a secondary light source, the secondary light source having a very close center wavelength and line-width to the anti-Stokes band 21 of the primary light source. In other embodiments, a secondary light source whose scattered Stoke band 25 coincides with the anti-Stoke band of the primary light source 21 may be used, as shown in FIG. 5. The light source of similar intensity and line-width may improve the accuracy of the compensation.

Figure 6:
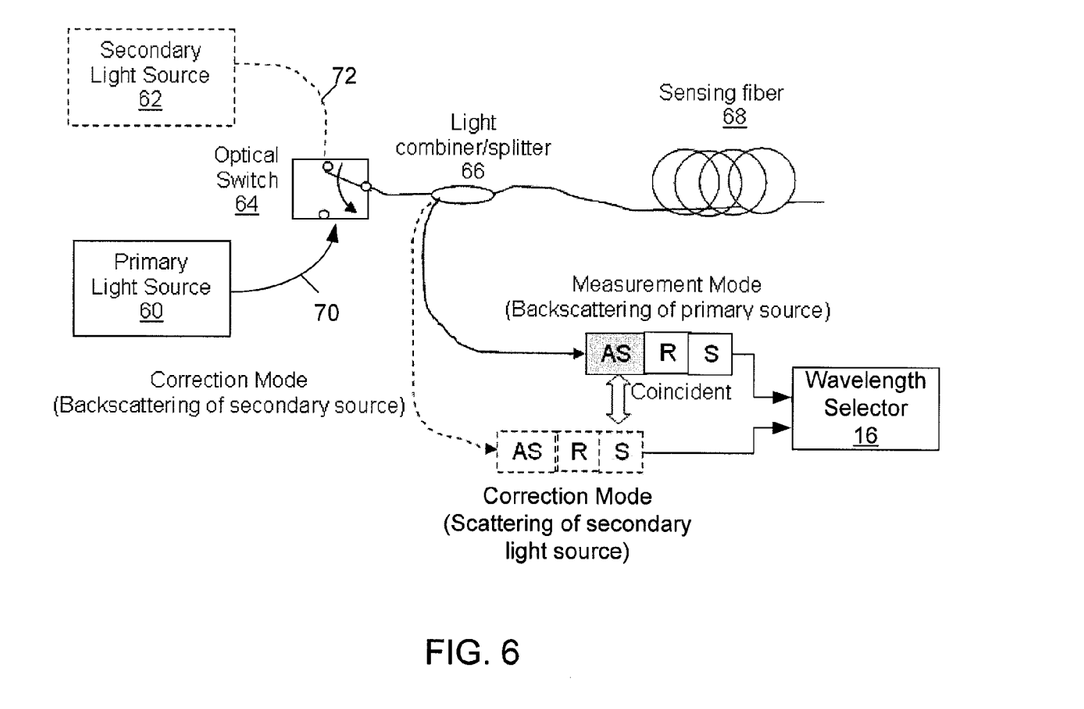
FIG. 6 shows a block diagram of a calibration system, in accordance with embodiments of the disclosure.

FIG. 6 illustrates an auto-calibration system, according to embodiments of the present disclosure. The primary light source 60 of the DTS may inject optical energy into the sensing fiber 68 through the optical route 70 via light combiner/splitter 66. Scattering bands Stokes (S), Rayleigh (R), and anti Stokes (AS) may be obtained and may be used to calculate a temperature profile.

The anti-Stokes band generated from primary light source 60 is varied by other physical phenomena and thus, may cause an error in the temperature calculations. According to one embodiment, during a correction mode, optical switch 64 may be changed such that an energy path from secondary light source 62 via optical route 72 may be created. The selected secondary light source may generate a Stokes backscattering band identical to or substantially similar to the anti-Stokes band of the primary light source 60.

In some embodiments, the primary light source and the secondary light source may be the light source, i.e., a dual wavelength laser source operably configured to provide at least two optical signals to the sensing fiber. One of ordinary skill in the art may recognize that an optical switch may not be needed. The dual wavelength laser source may operate at a first wavelength and at least the anti-Stokes band may be collected. Next, the dual wavelength laser source may operate at a second wavelength and at least the Stokes band may be collected, where the anti-Stokes and Stokes band are substantially similar.

Referring to Table 1, an example of a first light source and second light source are shown. The selection of a secondary light source may be based on its Stokes band in proximity to the anti-Stokes (A-Stokes) band of the primary light source. 980 nm semiconductor laser sources, which can be used as a secondary light source are popularly used as a pumping source of high fiber lasers and are commercially available.

| Light Source | Wavelength, λ (nm) | Δλ (nm) | A-Stokes | Stokes |
|---|---|---|---|---|
| Primary Light Source | 1064 | 45.3 | 1018.7 | 1109.3 |
| Secondary Light Source | 980 | 38.4 | 941.6 | 1018.4 |

Δλ indicates the Raman Stokes or anti-Stokes separation from the primary light source's center wavelength. Each bandwidth may be extended over, for example, 20 nm although the range may be greater or less than 20 nm. One of ordinary skill in the art can recognize that other primary light sources may be used as long as the secondary light source's Stokes band is substantially similar to the anti-Stokes band of the primary light source.

The secondary light source's Stokes attenuation profile, without or with the minimum temperature effect, may be used to correct the anti-Stokes profile made by the primary light source during a measurement mode. Thus, the generation of an extra wavelength band via a second light source that may be insensitive to temperature effects and corresponds to an anti-Stokes band of the DTS unit (e.g., primary light source) may be used to correct temperature error induced by anti-Stokes profile in the first primary light source.

Figure 7A:
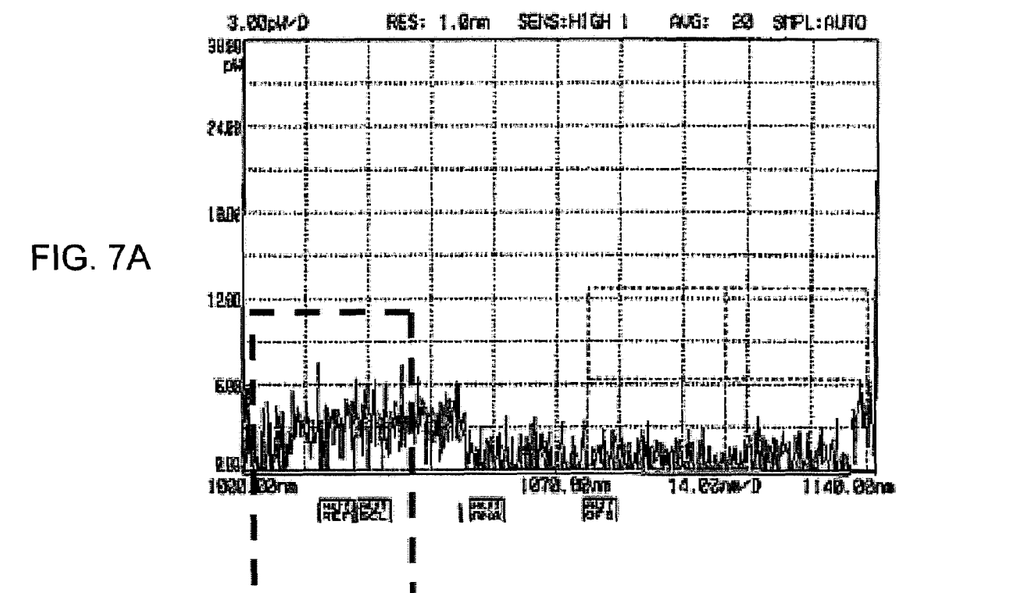
FIGS. 7A and 7B show a profile of an anti-Stokes band of a primary light source and a Stokes band of a secondary light source, in accordance with embodiments of the disclosure.
Figure 7B:
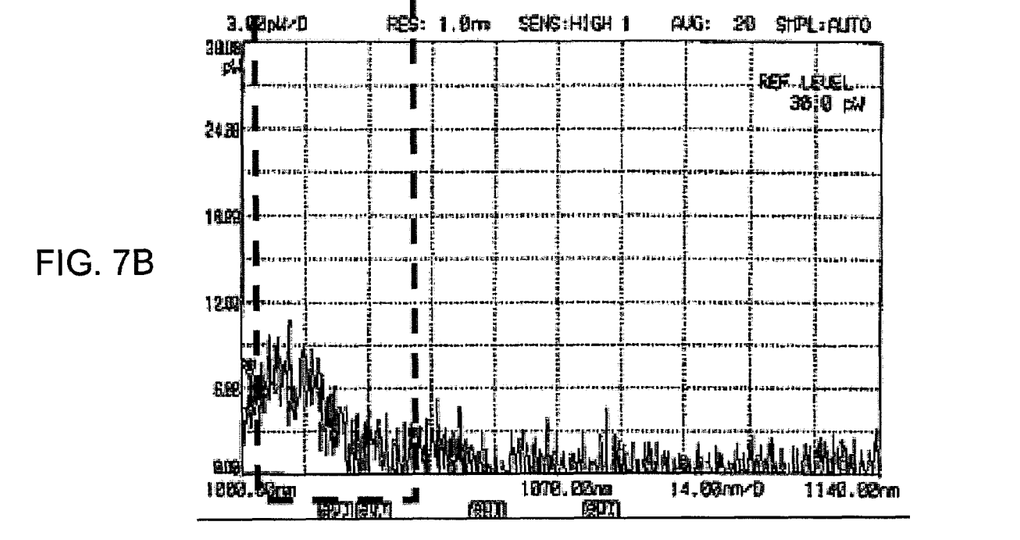

Two like bands, one from the anti-Stokes of a primary light source (in measurement mode) and the other from the Stokes band of the secondary light source (in correction mode) may pass through a wavelength selector 16 (FIG. 6) and may be detected with an Optical Spectrum Analyzer. The result is shown in FIGS. 7A and 7B. The wavelength bands under the dotted area may indicate the anti-Stokes band for the primary light source (FIG. 7A) and the Stokes band of the secondary light source (FIG. 7B).

Figure 8:
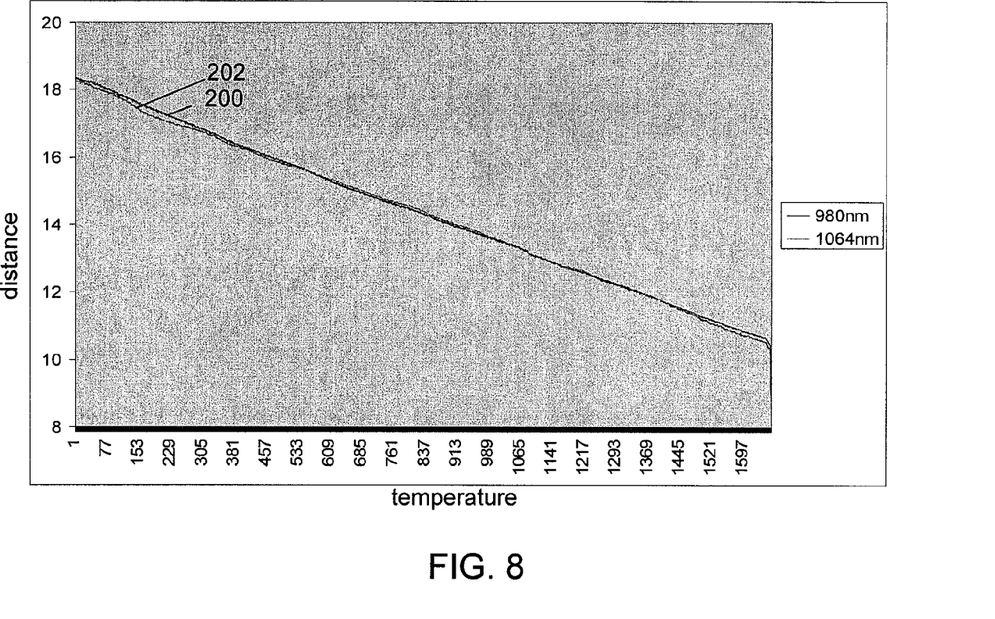
FIG. 8 shows a profile of a primary light source and a second light source, in accordance with embodiments of the disclosure.
Figure 9:
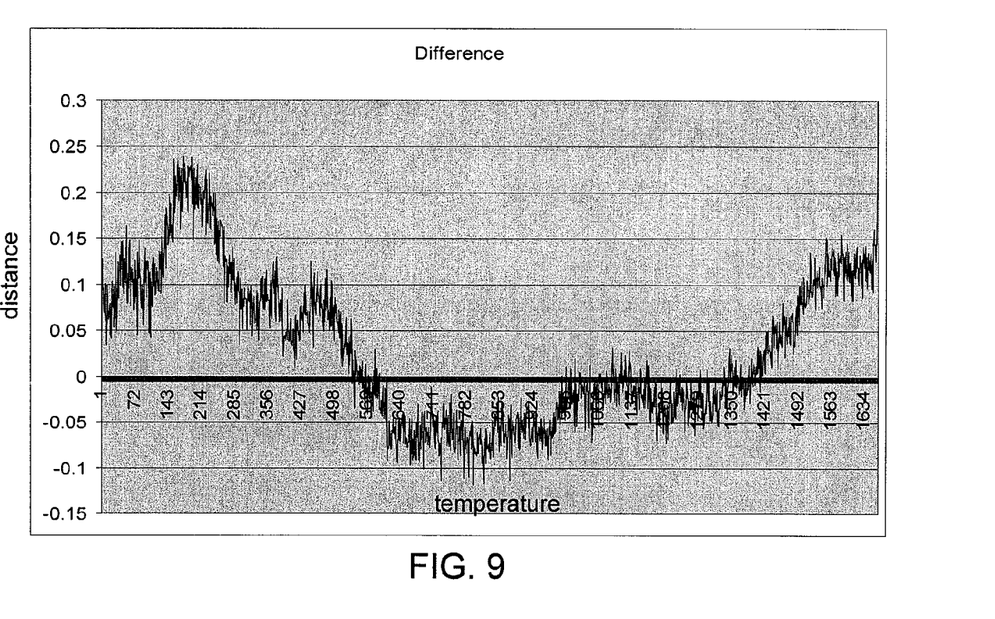
FIG. 9 shows the difference between the primary light source and the second light source profile of FIG. 8, in accordance with embodiments of the disclosure.

FIG. 8 show the profile of the primary anti-Stokes band (202) and the secondary Stoke band (200), and FIG. 9 shows the difference between the two profiles, which will be used as a calibration factor, respectively.

Figure 10:
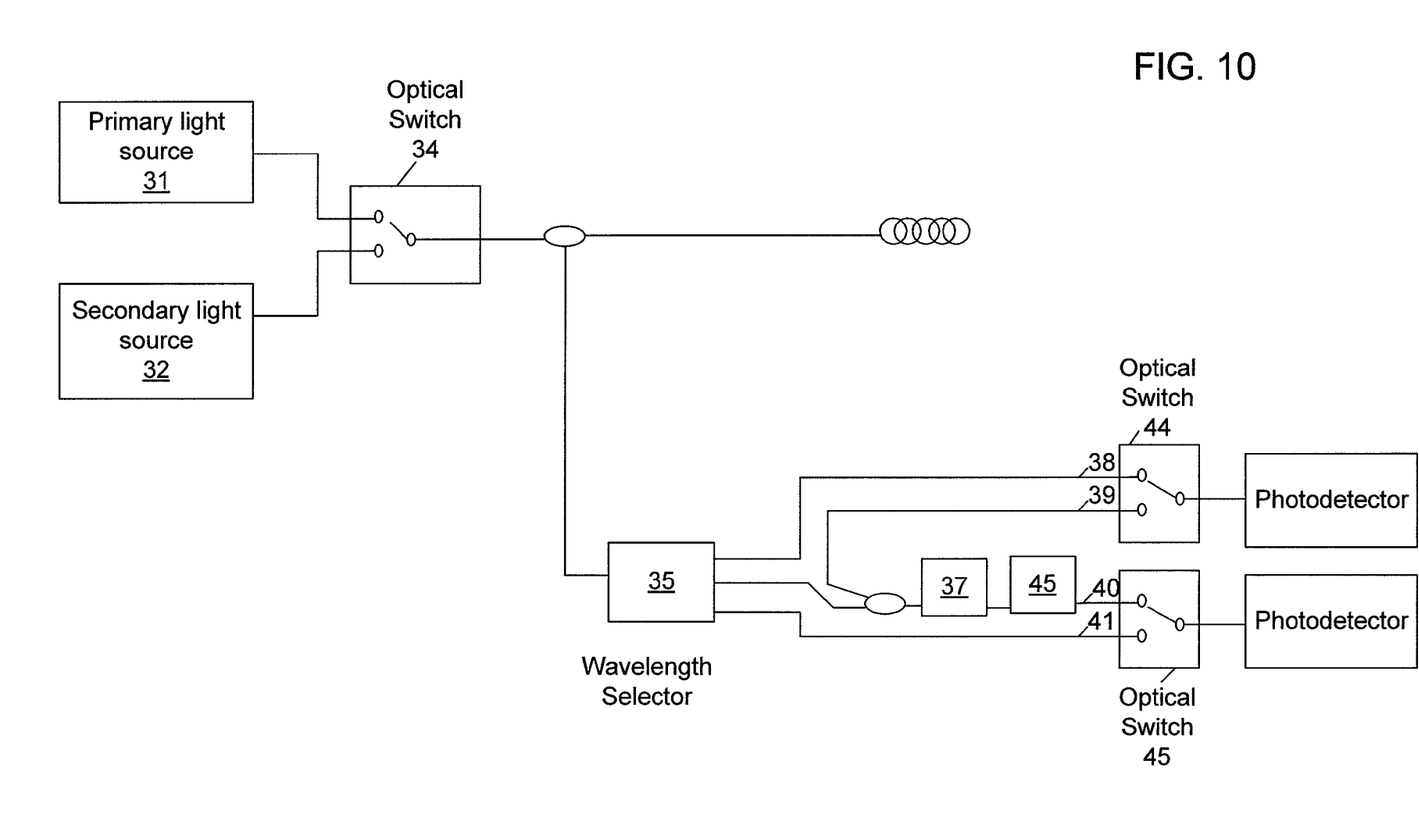
FIG. 10 shows a block diagram of a calibration system, in accordance with embodiments of the disclosure.

Referring to FIG. 10, an alternative calibration system is shown. By selecting the primary and secondary light source 31 and 32 via an optical switch 34, which may be synchronized to optical switches 44 and 45, the Rayleigh and the anti-Stokes bands which are outputs of wavelength selector 35 (38, 39, and 41 respectively) of the primary may be chosen to calculate the temperature profile in measurement mode. In one respect, outputs 38 and 40 may be used during a measurement mode and outputs 39 and 41 may be used during a calibration mode.

During calibration mode, the secondary Rayleigh band and the Stokes band (output 39 and 40 of the optical switches 44 and 45) may be selected to calibrate the primary anti-Stokes and the Rayleigh (e.g., 980 nm and 1015 nm). Unit 37 and 45 may be wavelength reflection devices such as a FBG (Fiber Bragg grating) and edge filter respectively. By implementation of this configuration, the anti-Stokes and the DAF (Differential Attenuation factor) between the sources 1064 and 980 may also be calculated. The DAF may be determined based on the attenuation difference between the primary light source and the secondary light source. In other words, the difference between the anti-Stoke bands of the primary light source and the Stokes band of the secondary source may be used to determine the DAF.

Various advantages of fiber optic sensors make them useful as tools particularly for application in electric power industries. Small size, flexibility, and immunity to EMI (Electromagnetic Interference) are the key benefits. The disclosure provides systems and methods for the detection, location, and measurement of corrosion along a length of an extended object or objects on which a single line of optical fiber is deployed in close proximity.

In some respect, a distributed sensor system and method for detecting, locating, and measuring corrosion occurring anywhere in the vicinity of an optical fiber containing an appropriate luminescent material are provided. The system and method may provide time rate progress data for the entire length or at discrete points of the line.

Figure 11:
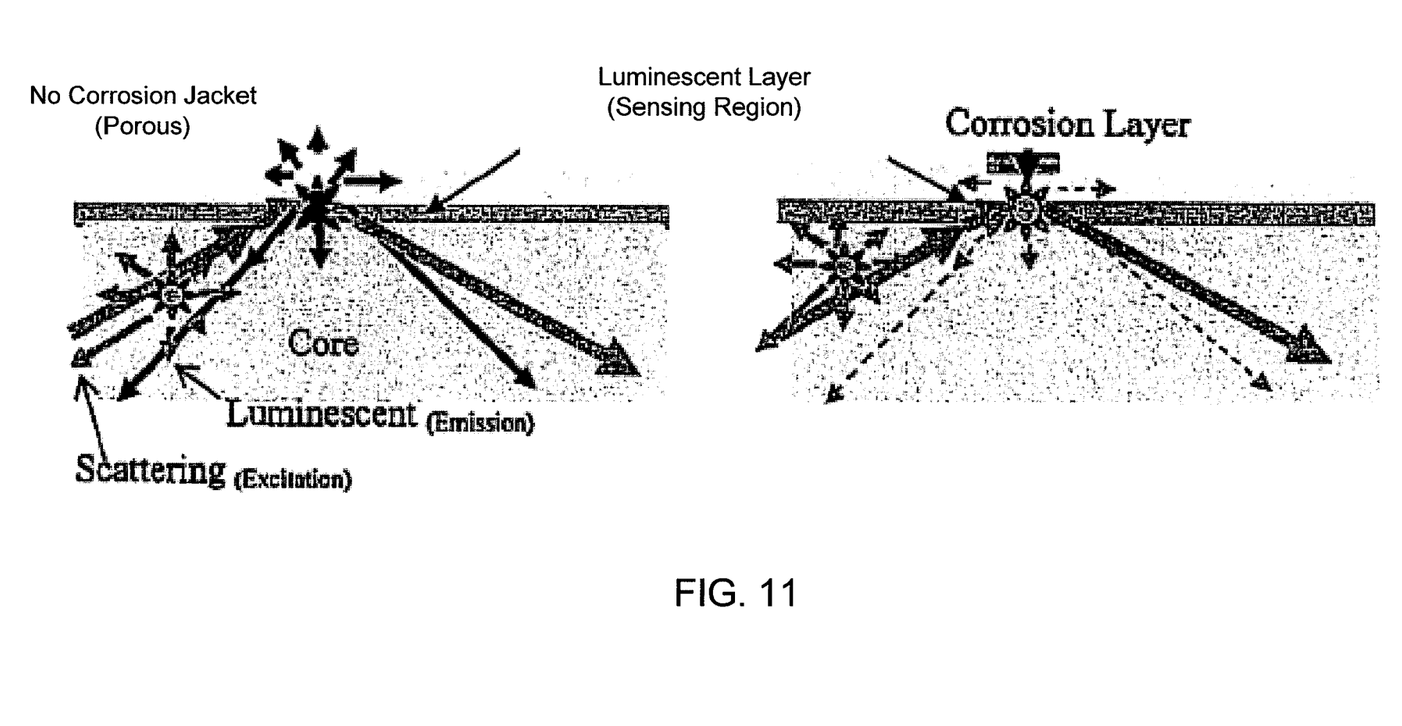
FIG. 11 shows a block diagram for detecting corrosion, in accordance with embodiments of the disclosure.

In one respect, the sensor of the present disclosure may utilize optical fiber, which contains continuous or discrete luminescent layers. When corrosion occurs, the luminescent material starts to interact with corrosion chemicals and the luminescent material's emissions may change, for example, in intensity and/or peak wavelength. A back scattered emission light from the sensing region may be guided to a detector through the fiber as shown in FIG. 11. By selecting a suitable luminescent material, the corrosion effects may be effectively monitored.

Figure 12A:
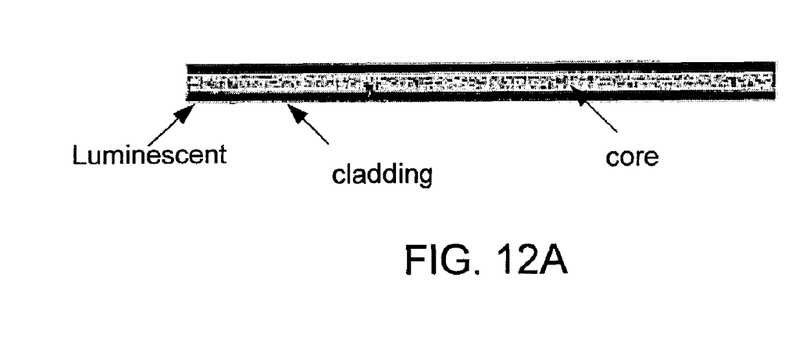
FIGS. 12A-12D show integration of a luminescent layer on a fiber, in accordance with embodiments of the disclosure.
Figure 12B:
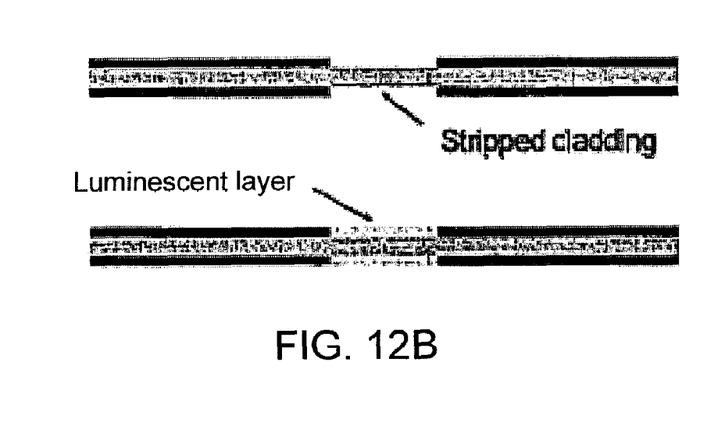
Figure 12C:
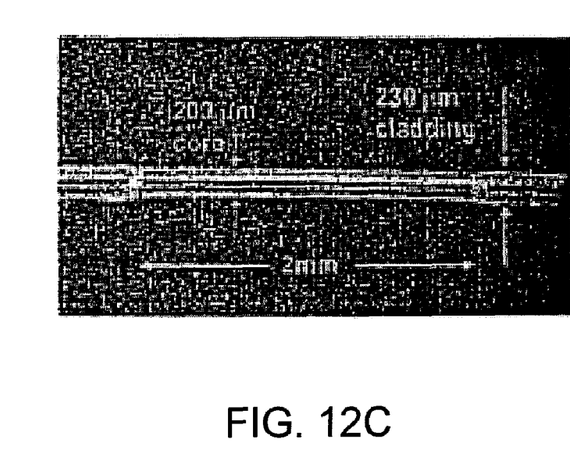
Figure 12D:
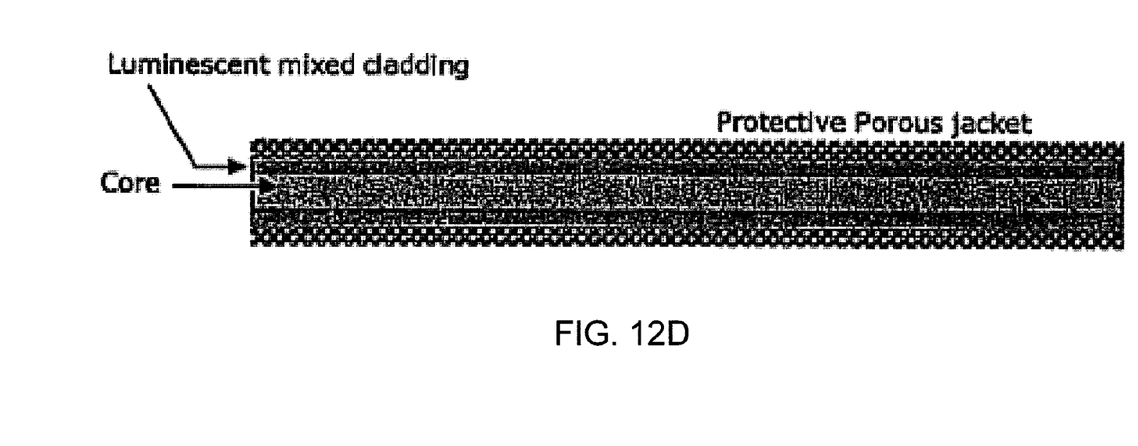

The luminescent material may be integrated onto the entire length of the core (FIG. 12A) or at discrete locations on the core, as shown in FIGS. 12B and 12C. Alternatively, a porous protection layer is integrated on luminescent cladding layer as the jacket of the fiber, as shown in FIG. 12D.

Figure 13:
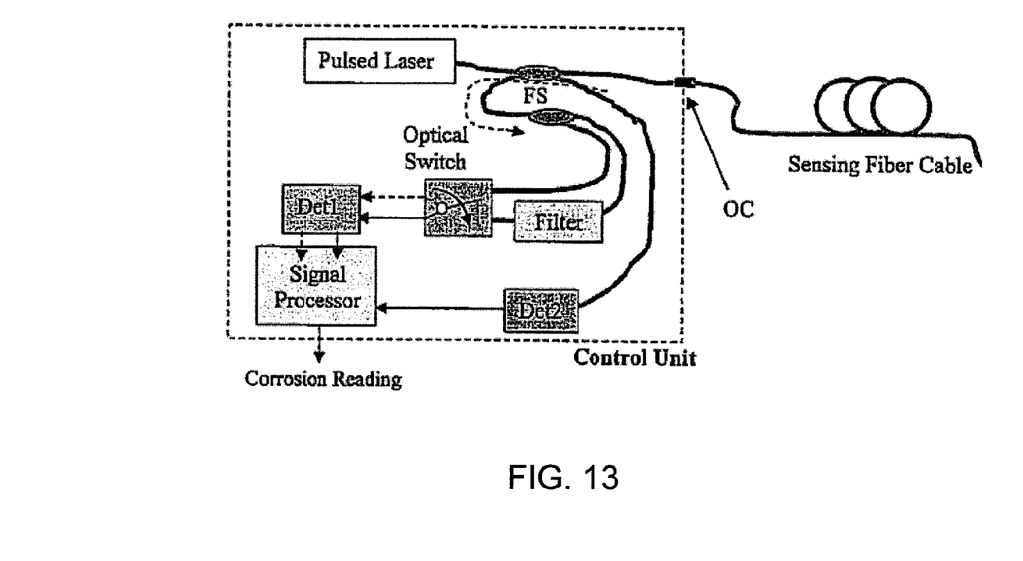
FIG. 13 shows a block diagram of a system, in accordance with embodiments of the disclosure.

In some respect, the flight time of the light pulse may used to determine the location of the corrosion source along the fiber, using for example a sensing system as shown in FIG. 13. The system may include a pulsed laser coupled to a fiber splitter (FS) which may be coupled to an optical connector (OC). It is noted that a pulsed or CW ultra violet laser may be used to find a corrosion location. Alternatively, any electromagnetic radiation source may be used. The intensity variation of the lighting source, connector, and/or sensing fiber may be compensated.

Coupled to the optical connector may be a sensing fiber which may be illuminated by the radiation source and may provide backscattering emission light via the OC and to, for example, the filter or a detector (Det2). Alternatively, the backscattering emission light may be provided to a filter and an optical switch, the optical switch and filter may be coupled a detector (Det 1). Outputs from Det1 and Det2 may be provided to a signal processor for determining, among other things, corrosion location.

By measuring the average signal from backscattered emission light, the magnitude of the corrosion can also be determined. A compensating algorithm may be used to avoid calculation error due to undesired variation of backscattered light intensities and to avoid the calculation error due to undesired variation of backscattered light intensities occurring from the fiber connector, bending of sensing fiber itself and the light source.

Figure 14A:
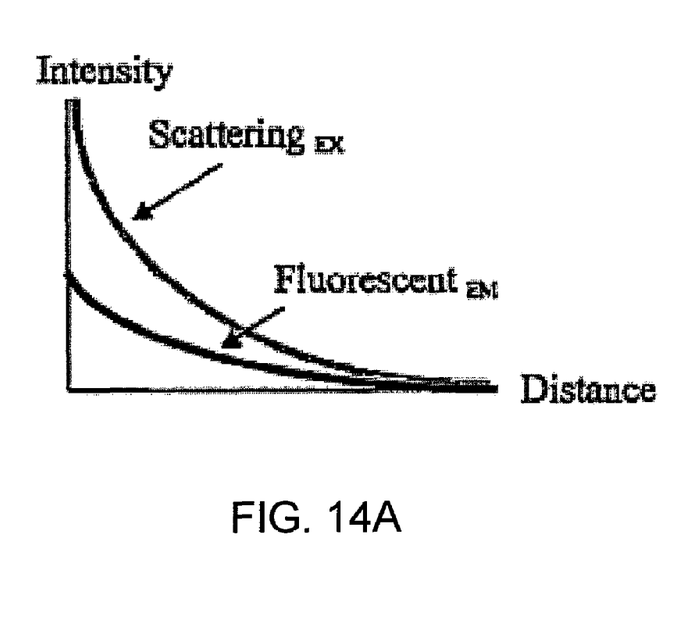
FIGS. 14A and 14B show an output of the system of FIG. 13 indicating where corrosion has occurred, in accordance with embodiments of the disclosure.
Figure 14B:
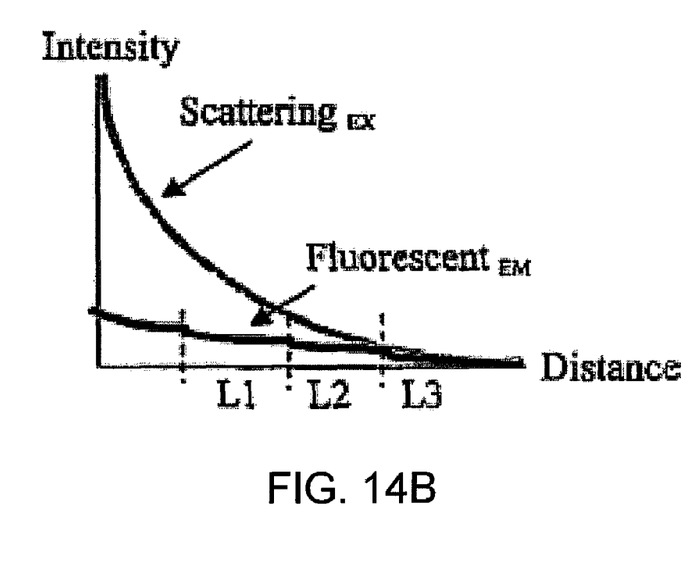

When corrosion occurs in proximity to the area where the sensing fiber is deployed, the backscattered light luminescent intensity may be affected at each location, as illustrated in the graphs of FIG. 14A and FIG. 14B. In FIG. 14A, no corrosion was detected. In FIG. 14B, incidents of corrosion occurred at locations, L1, L2, and L3.

It is noted that the present disclosure contemplates using other backscattering bands from at least one light source to calibrate a temperature sensing system. The anti-Stokes and Stokes band from a first light source and a second light source, respectively are examples of the bands that may be used. One of ordinary skill in the art can recognize the advantages of replacing a backscattering band from a first light source due to perturbations or factors with a similar backscattering band from another light source.

With the benefit of the present disclosure, those having ordinary skill in the art will comprehend that techniques claimed here may be modified and applied to a number of additional, different applications, achieving the same or a similar result. The claims cover all such modifications that fall within the scope and spirit of this disclosure.

The invention claimed is:

1. A method for automatic calibration of temperature measurement during a measurement mode in a system using a fiber optic distributed sensor comprising the steps of:
 a. in a measurement mode providing a primary light source light pulse energy into a sensing fiber by selection using an optical switch;
  i. collecting backscattered Raman Stokes and anti-Stokes light components;
  ii. calculating temperatures using the intensities of the backscattered Raman Stokes and anti-Stokes light components;
 b. during a correction mode selecting with the optical switch a secondary light source and providing pulses of said secondary light source to the sensing fiber;
  i. collecting a backscattered Raman Stokes component of that secondary light source;
  ii. using the Raman Stokes component collected from the secondary light source in said correction mode to correct a Raman anti-Stokes profile collected from the primary light source while in measurement mode; and
  iii. calculating a corrected temperature from the corrected Raman anti-Stokes profile;
 c. wherein the primary light source and secondary light source are chosen so that a backscattered anti-Stokes band of said primary light source is substantially the same as a backscattered Stokes band of said secondary light source.

2. The method for automatic calibration of temperature measurement during a measurement mode in a system using a fiber optic distributed sensor of claim 1 wherein said primary light source and said secondary light source are provided by a multiple wavelength laser source configured to provide at least two optical signals.

3. The method for automatic calibration of temperature measurement during a measurement mode in a system using a fiber optic distributed sensor of claim 2 wherein said multiple wavelength laser source is configured to deliver two different wavelengths chosen so that the backscattered anti-Stokes band of the first is substantially the same as the backscattered Stokes band of the second.

* * * * *